(12) United States Patent
Morita et al.

(10) Patent No.: US 11,654,125 B2
(45) Date of Patent: May 23, 2023

(54) AGENT FOR ELEVATING NITRIC OXIDE CONCENTRATION

(71) Applicant: KYOWA HAKKO BIO CO., LTD., Tokyo (JP)

(72) Inventors: Masahiko Morita, Tokyo (JP); Ayako Kamimura, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 0 days.

(21) Appl. No.: 14/762,108

(22) PCT Filed: Jan. 21, 2014

(86) PCT No.: PCT/JP2014/051102
§ 371 (c)(1),
(2) Date: Jul. 20, 2015

(87) PCT Pub. No.: WO2014/112641
PCT Pub. Date: Jul. 24, 2014

(65) Prior Publication Data
US 2015/0352067 A1 Dec. 10, 2015

(30) Foreign Application Priority Data
Jan. 21, 2013 (JP) .............................. JP2013-008239

(51) Int. Cl.
*A61K 31/198* (2006.01)
*A61K 38/06* (2006.01)

(52) U.S. Cl.
CPC .......... *A61K 31/198* (2013.01); *A61K 38/063* (2013.01)

(58) Field of Classification Search
None
See application file for complete search history.

(56) References Cited

U.S. PATENT DOCUMENTS

| | | | | |
|---|---|---|---|---|
| 5,204,114 A * | 4/1993 | Demopoulos | .......... | A61K 9/145 424/451 |
| 5,922,345 A * | 7/1999 | Horrobin | ............ | A61K 31/202 424/439 |
| 6,159,500 A | 12/2000 | Demopoulos et al. | | |
| 6,444,432 B1 * | 9/2002 | Kleinfeld | | |
| 10,094,031 B2 * | 10/2018 | Fukumoto | ............ | C07K 5/0215 |
| 10,640,532 B2 * | 5/2020 | Ooshima | ................ | B01D 9/005 |
| 10,774,109 B2 * | 9/2020 | Fukumoto | ............ | A61K 38/06 |
| 10,858,393 B2 * | 12/2020 | Fukumoto | ............ | A61P 1/16 |
| 2005/0192210 A1 | 9/2005 | Rothbard et al. | | |
| 2005/0192229 A1 * | 9/2005 | Perricone | ............ | A61K 38/063 514/18.7 |
| 2006/0099244 A1 * | 5/2006 | Guilford | ................ | A61K 9/127 424/450 |
| 2006/0189603 A1 | 8/2006 | Garvey et al. | | |
| 2007/0259024 A1 | 11/2007 | Furukawa et al. | | |
| 2010/0197577 A1 | 8/2010 | Horiba et al. | | |
| 2011/0129523 A1 * | 6/2011 | Guilford | ................ | A61K 9/127 424/450 |

FOREIGN PATENT DOCUMENTS

| | | |
|---|---|---|
| CN | 1408427 A | 4/2003 |
| CN | 1748785 A | 3/2006 |
| CN | 101027078 A | 8/2007 |
| CN | 101703813 A | 5/2010 |
| JP | H04-074135 A | 3/1992 |
| JP | 2001-507696 A | 6/2001 |
| JP | 2008-531579 A | 8/2008 |
| WO | WO 1997/016983 A1 | 5/1997 |
| WO | WO 2008/129851 A1 | 10/2008 |
| WO | WO 2013/122188 A1 | 8/2013 |

OTHER PUBLICATIONS

Hien et al. (Southern Fruit Research Institute). [Online]. "Analysis of Pomelo Value Chain in Ben Tre Province". Retrieved from the Internet: <URL: http://www.sme-gtz.org.vn/Portals/0/AnPham/16-%20Analysis%20of%20Pomelo%20VC%20in%20Ben%20Tre%20province-ENG.pdf>. pp. 1-28.*
Haas et al. "Exercise Training and Peripheral Arterial Disease". Comprehensive Physiology. 2012; 2:2933-3017. (Year: 2012).*
Brass et al. "Acquired Skeletal Muscle Metabolic Myopathy in Atherosclerotic Peripheral Arterial Disease". Vascular Medicine. 2000; 5:55-59. (Year: 2000).*
Adachi et al., *British Journal of Pharmacology*, 129: 1014-1020 (2000).
Arjinpathana et al., *Journal of Dermatological Treatment*, 23: 97-102 (2012).
Cheung et al., *American Journal of Physiology—Heart and Circulatory Physiology*, 273(3—part 2): H1231-H1238 (1997).
Fujii et al., *Japan Food Science*, 39(9): 67-73 (2000).
Hayashi et al., *PNAS*, 102(38): 13681-13686 (2005).
Ochiai et al., *International Journal of Cardiology*, 155(2): 257-261 (2012).
Sugimura et al., *Journal of Nutritional Science & Vitaminology*, 44: 613-624 (1998).
Vanhatalo et al., *Journal of Physiology*, 15: 5517-5528 (2011).
Japanese Patent Office, International Search Report in International Patent Application No. PCT/JP2014/051102 (dated Apr. 22, 2014).
Ghigo et al., *Amino Acids*, 10: 277-281 (1996).
Prasad et al., *Journal of the American College of Cardiology*, 34(2): 507-514 (1999).

(Continued)

*Primary Examiner* — Savitha M Rao
*Assistant Examiner* — Gregg Polansky
(74) *Attorney, Agent, or Firm* — Leydig, Voit & Mayer, Ltd.

(57) ABSTRACT

An agent for elevating nitric oxide (NO) concentration comprising glutathione or a salt thereof as an active ingredient; an agent for elevating NO concentration comprising glutathione or a salt thereof as an active ingredient for preventing or ameliorating a vascular endothelial malfunction-related symptom, or dilating blood vessels or promoting blood flow by elevating NO concentration; and a method for elevating NO concentration by ingesting glutathione or a salt thereof.

4 Claims, 2 Drawing Sheets

(56) References Cited

OTHER PUBLICATIONS

Zhijun et al., *Chinese Journal of Hypertension*, 20(12): 1181-1184 (2012).
Chinese Patent Office, Notification of First Office Action in Chinese Patent Application No. 201480005570.8 (dated Aug. 12, 2016).
Kerksick et al., *Journal of the International Society of Sports Nutrition*, 2(2): 38-44 (2005).
Misner, Bill, "Intravenous Glutathione Enhances Cycling Time Trial Performance (A Case Study)," originally published as "Does Glutathione Enhance Exercise Performance?—A Case Study," *The Townsend Letter For Doctors & Patients*, pp. 66-68 (Jul. 2003) [as retrieved from the Internet at URL https://www.hammernutrition.com/downloads/glutathione_tt.pdf on Nov. 24, 2016].
European Patent Office, Partial Supplementary European Search Report in European Patent Application No. 14740411.5 (dated Dec. 9, 2016).
Martina et al., "Administration of glutathione in patients with type 2 diabetes mellitus increases the platelet constitutive nitric oxide synthase activity and reduces PAI-1," *J. Endocrinol. Invest.*, 24: 37-41 (2001).
Canadian Intellectual Property Office, Office Action in Canadian Patent Application No. 2,898,416 (dated Sep. 23, 2019).
Aronow et al., "Prevalence of Coexistence Artery Disease, Peripheral Arterial Disease, and Atherothrombotic Brain Infarction in Men and Women ≥ 62 Years of Age," *Am. J. Cardiol.*, 74(1): 64-65 (1994).
Chanséaume et al., "Potential Mechanisms of Muscle Mitochondrial Dysfunction in Aging and Obesity and Cellular Consequences," *Int. J. Mol. Sci.*, 10(1): 306-324 (2009).
Zizola et al., "Metabolic and structural impairment of skeletal muscle in heart failure," *Heart Fail. Rev.*, 18(5): 623-630 (2013).
Ghigo et al, "Nitric oxide synthesis is impaired in glutathione-depleted human umbilical vein endothelial cells," *Am. J. Physiol.*, 265(3): C728-C732 (1993).
China National Intellectual Property Administration, The Fourth Office Action in Chinese Patent Application No. 201480005570.8 (dated Dec. 23, 2021).
Atakishi et al., "Effects of Reduced Glutathione on Nitric Oxide Level, Total Antioxidant and Oxidant Capacity and Adenosine Deaminase Activity," *Eur. Rev. Med. Pharmacol. Sci.*, 14(1): 19-23 (2014).
Henry, "Mechanisms of Changes in Basal Metabolism During Ageing," *Eur. J. Clin. Nutr.*, 54(Suppl 3): S77-S91 (2000).

* cited by examiner

AGENT FOR ELEVATING NITRIC OXIDE CONCENTRATION

CROSS-REFERENCE TO RELATED APPLICATIONS

This patent application is the U.S. national phase of International Patent Application No. PCT/JP2014/051102, filed Jan. 21, 2014, which claims the benefit of Japanese Patent Application No. 2013-008239, filed on Jan. 21, 2013, which are incorporated by reference in their entireties herein.

TECHNICAL FIELD

The present invention relates to an agent for elevating nitric oxide (NO) concentration comprising glutathione or a salt thereof as an active ingredient, in which prevention or amelioration of a vascular endothelial malfunction-related symptom, or vasodilation and blood flow-promoting effects through a higher NO concentration elevating action in vivo can be expected.

BACKGROUND ART

NO is a gaseous substance having various physiological functions as a signal. NO produced from vascular endothelial cells is called an endothelium-derived relaxing factor (EDRF), and has various physiological activities for maintaining normal vascular function, such as a blood vessel relaxation action, an oxidized LDL inhibitory action, a platelet aggregation inhibition action, an anti-smooth muscle cell proliferation action, and an anti-oxidative action (Non-Patent Document 1).

Arteriosclerosis is a state in which the elasticity of a vascular wall is reduced by hyperactivity of an inflammatory reaction in the vascular intima or accumulation of cholesterol. As a result, a smooth blood flow is less likely to be maintained, and thrombus is likely to be formed. As one of the factors, a decrease in the NO production ability of vascular endothelial cells has been pointed out by a number of studies. In this way, NO is a very important regulator for vascular function, and thus, studies to prevent or ameliorate a vascular endothelial malfunction such as arteriosclerosis have been proceeded by attempts to enhance the NO production ability of vascular endothelial cells (Non-Patent Documents 1 and 2). Further, in recent years, usefulness of NO in daily activities has been focused, and, for example, studies to increase the training efficiency by improving exercise performance, increasing oxygen consumption efficiency, or improving muscle metabolism by increasing the NO concentration in the body during exercise have been reported (Non-Patent Document 3). That is, by enhancing the NO production ability of vascular endothelial cells, in addition to the prevention or amelioration of an ischemic vascular disease due to a vascular endothelial malfunction such as arteriosclerosis, for example, increase in exercise efficiency or the like in daily activities can be expected.

Glutathione is a tripeptide consisting of glutamic acid, cysteine, and glycine, and glutathione plays a central role in a removal mechanism of the reactive oxygen species in vivo. Furthermore, glutathione is also involved in a detoxification mechanism by which xenobiotics are removed from the body. A hepatoprotective action (Non-Patent Document 4) and a whitening action (Non-Patent Document 5) by ingestion of glutathione have been reported. From such functionalities, glutathione is used as an antidote at the time of poisoning or medicine for improving liver function, or a food material for anti-oxidation.

So far, it has been reported that, when glutathione is administered intravenously to a human who is observed to have arteriosclerosis, the blood vessel relaxation response caused by acetylcholine administration which is an NO production stimulant in a vascular endothelium is enhanced (Non-Patent Document 6). In addition, it has been reported that, when a removed aorta of a rabbit was treated with a drug, the glutathione concentration in vascular tissues was lowered, and vasodilation was induced by addition of an NO donor, and thus the vasodilation action due to the NO donor was improved by combined addition of glutathione (Non-Patent Document 7).

However, these prior reports relate to studies performed under limited special experimental conditions such as a condition that the NO donor is externally added, a condition that a removed vessel is evaluated, or a condition that glutathione synthesis is inhibited and the endogenous glutathione concentration is depleted, and it has not been known at all that the NO concentration in vivo is increased by administration of only a glutathione substance into an animal.

RELATED ART

Non-Patent Document

[Non-Patent Document 1] "PNAS", Vol. 102, pp. 13681-13686, 2005
[Non-Patent Document 2] "International Journal of Cardiology", Vol. 155, pp. 257-261, 2012
[Non-Patent Document 3] "Journal of Physiology", Vol. 15, pp. 5517-5528, 2011
[Non-Patent Document 4] "Journal of Nutritional Science & Vitaminology", Vol. 44, pp. 613-624, 1998
[Non-Patent Document 5] "Journal of Dermatological Treatment", Vol. 23, pp. 97-102, 2012
[Non-Patent Document 6] "Journal of the American College of cardiology", Vol. 34, pp. 507-514, 1999
[Non-Patent Document 7] "British Journal of Pharmacology", Vol. 129, pp. 1014-1020, 2000

DISCLOSURE OF INVENTION

Problems to be Solved by the Invention

An object of the present invention is to provide an agent for elevating NO concentration which exhibits prevention or amelioration of a vascular endothelial malfunction-related symptom, or vasodilation and blood flow-promoting effects through a higher NO concentration elevating action in vivo, and is effective for prevention or amelioration of an ischemic disease, exercise performance improvement, muscle metabolism improvement, lipid accumulation suppression, skin quality improvement, memory and learning ability improvement, attention concentration improvement, shoulder stiffness amelioration, amelioration of excessive sensitivity to cold, or swelling suppression.

Means for Solving the Problems

The present invention relates to the following (1) to (24).
(1) An agent for elevating nitric oxide (NO) concentration, comprising glutathione or a salt thereof as an active ingredient.

(2) The agent for elevating NO concentration described in (1), which dilates blood vessels or promotes blood flow by elevating NO concentration.
(3) The agent for elevating NO concentration described in (1), which prevents or ameliorates a vascular endothelial malfunction-related symptom by elevating NO concentration.
(4) The agent for elevating NO concentration described in (2), which causes exercise performance improvement, muscle metabolism improvement, lipid accumulation suppression, skin quality improvement, memory and learning ability improvement, attention concentration improvement, shoulder stiffness amelioration, amelioration of excessive sensitivity to cold, or swelling suppression, by dilating the blood vessel or promoting the blood flow.
(5) The agent for elevating NO concentration described in (3), wherein the vascular endothelial malfunction-related symptom is at least one symptom of an ischemic disease selected from cerebral infarction, myocardial infarction, angina, peripheral arterial occlusion, pulmonary hypertension, renal dysfunction, retinopathy, and sexual dysfunction.
(6) The agent for elevating NO concentration described in any one of (1) to (5), wherein the glutathione or a salt thereof is reduced glutathione or a salt thereof, or/and oxidized glutathione or a salt thereof.
(7) A method for elevating NO concentration, comprising a step of having a subject in need of elevating the NO concentration ingest glutathione or a salt thereof in a sufficient amount to elevate the NO concentration of the subject or administering glutathione or a salt thereof in the sufficient amount to the subject.
(8) The method for elevating NO concentration described in (7), wherein blood vessels are dilated or blood flow is promoted by elevating the NO concentration.
(9) The method for elevating NO concentration described in (7), wherein a vascular endothelial malfunction-related symptom is prevented or ameliorated by elevating the NO concentration.
(10) The method for elevating NO concentration described in (8), wherein exercise performance improvement, muscle metabolism improvement, lipid accumulation suppression, skin quality improvement, memory and learning ability improvement, attention concentration improvement, shoulder stiffness amelioration, amelioration of excessive sensitivity to cold, or swelling suppression is caused by dilating the blood vessel or promoting the blood flow.
(11) The method for elevating NO concentration described in (9), wherein the vascular endothelial malfunction-related symptom is at least one symptom of an ischemic disease selected from cerebral infarction, myocardial infarction, angina, peripheral arterial occlusion, pulmonary hypertension, renal dysfunction, retinopathy, and sexual dysfunction.
(12) The method for elevating NO concentration described in any one of (7) to (11), wherein the glutathione or a salt thereof is reduced glutathione or a salt thereof, or/and oxidized glutathione or a salt thereof.
(13) Glutathione or a salt thereof, which is for use in elevating internal NO concentration of a subject which ingests the glutathione or the salt thereof or to which the glutathione or the salt thereof is administered.
(14) The glutathione or a salt thereof described in (13), which is for use in dilating blood vessels or promoting blood flow by elevating the internal NO concentration of the subject which ingests the glutathione or the salt thereof or to which the glutathione or the salt thereof is administered.
(15) The glutathione or a salt thereof described in (13), which is for use in preventing or ameliorating a vascular endothelial malfunction-related symptom by elevating the internal NO concentration of the subject which ingests the glutathione or the salt thereof or to which the glutathione or the salt thereof is administered.
(16) The glutathione or a salt thereof described in (14), which is for use in causing exercise performance improvement, muscle metabolism improvement, lipid accumulation suppression, skin quality improvement, memory and learning ability improvement, attention concentration improvement, shoulder stiffness amelioration, amelioration of excessive sensitivity to cold, or swelling suppression, by dilating the blood vessels or promoting the blood flow.
(17) The glutathione or a salt thereof described in (15), wherein the vascular endothelial malfunction-related symptom is at least one symptom of an ischemic disease selected from cerebral infarction, myocardial infarction, angina, peripheral arterial occlusion, pulmonary hypertension, renal dysfunction, retinopathy, and sexual dysfunction.
(18) The glutathione or a salt thereof described in any one of (13) to (17), wherein the glutathione or a salt thereof is reduced glutathione or a salt thereof, or/and oxidized glutathione or a salt thereof.
(19) Use of glutathione or a salt thereof for the manufacture of an agent for elevating NO concentration.
(20) The use of glutathione or a salt thereof described in (19), which is for the manufacture of an agent for elevating NO concentration which dilates blood vessels or promotes blood flow by elevating the NO concentration.
(21) The use of glutathione or a salt thereof described in (19), which is for the manufacture of an agent for elevating NO concentration which prevents or ameliorates a vascular endothelial malfunction-related symptom by elevating the NO concentration.
(22) The use of glutathione or a salt thereof described in (20), which is for the manufacture of an agent for elevating NO concentration which causes exercise performance improvement, muscle metabolism improvement, lipid accumulation suppression, skin quality improvement, memory and learning ability improvement, attention concentration improvement, shoulder stiffness amelioration, amelioration of excessive sensitivity to cold, or swelling suppression, by dilating the blood vessel or promoting the blood flow.
(23) The use of glutathione or a salt thereof described in (21), wherein the vascular endothelial malfunction-related symptom is at least one symptom of an ischemic disease selected from cerebral infarction, myocardial infarction, angina, peripheral arterial occlusion, pulmonary hypertension, renal dysfunction, retinopathy, and sexual dysfunction.
(24) The use of glutathione or a salt thereof according to described in any one of (19) to (23), wherein the glutathione or a salt thereof is reduced glutathione or a salt thereof, or/and oxidized glutathione or a salt thereof.

Effects of the Invention

The agent for elevating NO concentration according to the present invention comprises glutathione or a salt thereof as an active ingredient, and thus, both short-term and long-term administration are possible, and in particular, in the case of health-promoting food or the like or food ingested by focusing on a specific function of the present invention, ingestion is possible on a daily basis. In addition, since prevention or amelioration of a vascular endothelial malfunction-related symptom, or vasodilation and blood flow-promoting effects through an excellent NO concentration elevating action can be expected from the agent for elevating NO concentration according to the present invention, the agent can be applied to prevention or amelioration of an ischemic disease, exercise performance improvement, muscle metabolism improvement, lipid accumulation suppression, skin quality improvement, memory and learning ability improvement, attention concentration improvement, shoulder stiffness amelioration, amelioration of excessive sensitivity to cold, or swelling suppression.

EMBODIMENTS FOR CARRYING OUT THE INVENTION

Figure 1:
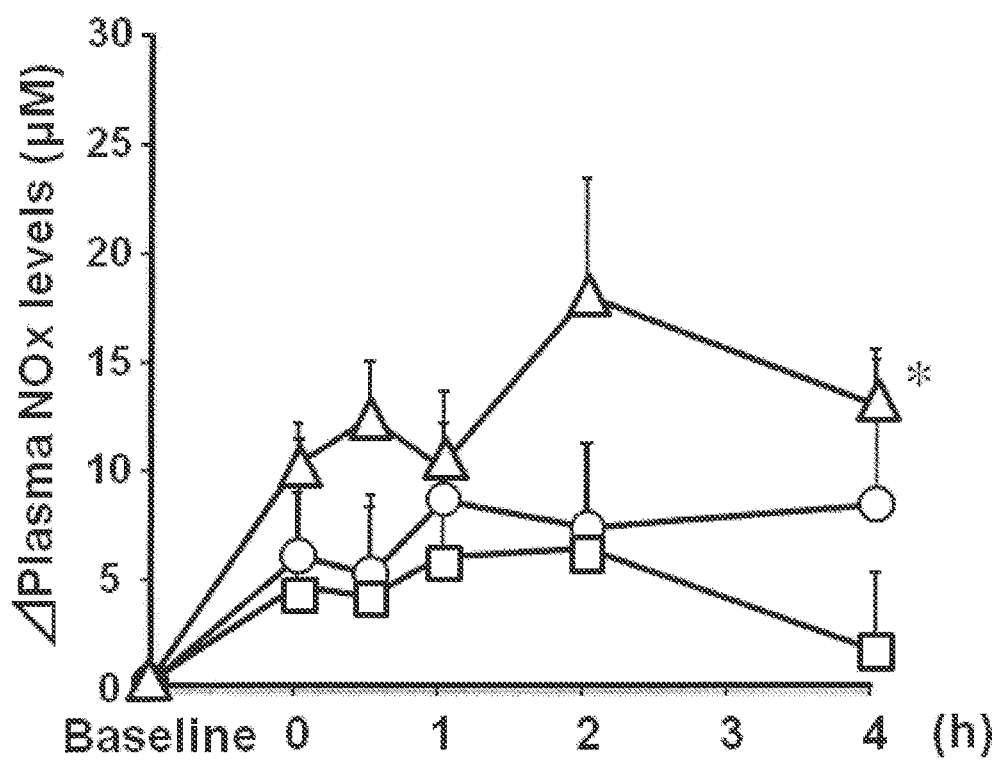
FIG. 1 shows an increase over time of an NOx concentration in blood after reduced glutathione is administered orally to rats. □ represents a control group, Δ represents a glutathione-50 mg/kg administered group, ○ represents a glutathione-25 mg/kg administered group, and * represents a significant difference at P<0.05.

The glutathione used in the present invention is reduced glutathione or oxidized glutathione.

The reduced glutathione represents a tripeptide having a structure of γ-L-Glu-L-Cys-Gly, and the oxidized glutathione represents a glutathione dipeptide in which two molecules of the reduced glutathione are bonded through a SS bond. The reduced glutathione and the oxidized glutathione used in the present invention may be obtained by any preparation method.

Examples of the preparation method of the reduced glutathione include methods such as an extraction method from microorganisms such as yeast [Methods in Enzymology, 3,603 (1957)], a chemical synthetic method [Bull. Chem. Soc. Jpn., 53, 2529 (1980)], and an enzymatic method (JP-A-61-074595), and examples of the preparation method of the oxidized glutathione include methods such as a method described in Acta Biochim. Pol., 17, 175 (1970). In addition, the reduced glutathione and the oxidized glutathione can also be obtained by purchasing them from Sigma-Aldrich Co. LLC. or the like.

The agent for elevating NO concentration according to the present invention may comprise any one of the reduced glutathione and the oxidized glutathione, or may comprise both the reduced glutathione and the oxidized glutathione. In addition, the reduced glutathione or the oxidized glutathione comprised in the agent for elevating NO concentration according to the present invention may be present in the agent as a salt. Examples of the salt of the reduced glutathione or the oxidized glutathione include acid addition salts, metal salts, ammonium salts, organic amine addition salts, and amino acid addition salts.

Examples of the acid addition salts include inorganic acid salts such as hydrochloride, sulfate, nitrate, and phosphate, and organic acid salts such as acetate, maleate, fumarate, citrate, malate, lactate, α-ketoglutarate, gluconate, and caprylate.

Examples of the metal salts include alkali metal salts such as a sodium salt and a potassium salt, alkaline earth metal salts such as a magnesium salt and a calcium salt, and an aluminum salt, and a zinc salt.

Examples of the ammonium salts include salts of ammonium and tetramethyl ammonium.

Examples of the organic amine addition salts include salts of morpholine and piperidine.

Examples of the amino acid addition salts include salts of glycine, phenylalanine, lysine, aspartic acid, and glutamic acid.

One or more types of the salts described above may be used in suitable combinations. In the present invention, substances which are metabolized into the reduced glutathione in vivo, for example, N-acetylcysteine or the like can also be used instead of glutathione.

Although, as the agent for elevating NO concentration according to the present invention, glutathione or a salt thereof as it is can be directly ingested or administered, usually, glutathione or a salt thereof is desirably provided as various product forms or formulations.

Although the product or formulation comprises glutathione or a salt thereof as an active ingredient, the product or formulation may further comprises any active ingredient. In addition, the product or formulation is manufactured by mixing the active ingredient together with one or more types of pharmaceutically acceptable carriers and by any method well known in the technical field of pharmaceutics.

As the ingestion or administration form of the product or formulation, it is desirable to use the most effective form when the NO concentration is increased in the body, and examples thereof include oral ingestion or oral administration, or, for example, parenteral administration such as intravenous administration, intraperitoneal administration, and subcutaneous administration; and, oral ingestion or oral administration is preferable.

The ingestion or administration form, or the dosage form may be, for example, any of oral agents such as a tablet, a powder, a granule, a pill, a suspension, an emulsion, an infusion•decoction, a capsule, a drink, a solution, an elixir, an extract, a tincture, and a fluid extract, and parenteral dosages such as an injection, a drop, a cream, and a suppository; and, an oral agent is suitably used.

A liquid preparation such as a drink, which is suitable for ingestion or oral administration, can be formulated by adding water, sugars such as sucrose, sorbitol, and fructose, glycols such as polyethylene glycol and propylene glycol, oils such as sesame oil, olive oil, and soybean oil, antiseptics such as p-hydroxy benzoic acid esters, paraoxybenzoic acid derivatives such as methyl paraoxybenzoate, preservatives such as sodium benzoate, flavors such as strawberry flavor and peppermint, or the like.

For example, a tablet, a powder, a granule, or the like, which is suitable for oral ingestion or administration, can be formulated by adding sugars such as lactose, saccharose, glucose, sucrose, mannitol, and sorbitol, starch such as potato, wheat, and corn, inorganic substances such as calcium carbonate, calcium sulfate, sodium hydrogen carbonate, and sodium chloride, excipients such as crystalline cellulose and vegetable powders including a licorice powder and a gentian powder, disintegrators such as starch, agar, a gelatin powder, crystalline cellulose, carmellose sodium, carmellose calcium, calcium carbonate, sodium hydrogen carbonate, and sodium alginate, lubricants such as magnesium stearate, talc, hydrogenated vegetable oil, macrogol, and silicone oil, binders such as polyvinyl alcohol, hydroxypropyl cellulose, methyl cellulose, ethyl cellulose, carmellose, gelatin, and a starch glue solution, surfactants such as fatty acid ester, plasticizers such as glycerin, or the like.

To the product form or formulation which is suitable for oral ingestion or administration, an additive generally used in foods and drinks, for example, sweeteners, colors, preservatives, thickening stabilizers, antioxidants, color formers, bleaching agents, anti-fungal agents, gum bases, bittering agents, enzymes, brightening agents, acidulants, seasonings, emulsifiers, toughening agents, agents for manufacture, flavors, spice extracts, or the like may be added.

The product form or formulation which is suitable for oral ingestion oral administration can be manufactured by processing into a tablet, a powder, a granule, a pill, a suspension, an emulsion, an infusion•decoction, a capsule, a drink, a solution, an elixir, an extract, a tincture, or a fluid extract of a unit packaging form per ingestion according to an ingestion period, the number of times of ingestion, or an ingestion amount.

For example, "a unit packaging form per ingestion" is a form in which the amount to be ingested per one time is predetermined, and "a unit packaging form per a week to three months" is a form in which the amount to be ingested for a week to three months is included. As the unit packaging form, examples thereof include a form in which a certain amount is defined by using a pack, a packaging, a bottle, or the like is exemplified.

For example, as "a unit packaging form per ingestion", in a case where the product form or formulation is a drink, examples thereof include a form in which a drink in which 10 mg or more of glutathione or a salt thereof is suspended or dissolved is put into a bottle or the like in a form of an amount to be drunk per ingestion.

For example, as "a unit packaging form per a week to three months", in a case where the ingestion amount per day, in one ingestion per day, is 300 mg, and a tablet comprises 50 mg of glutathione or a salt thereof, examples thereof include a form in which 42 tablets to 540 tablets are packaged.

For example, an injection suitable for parenteral administration is preferably formed of a sterilized aqueous agent comprising glutathione or a salt thereof which is isotonic to blood of a recipient. For example, in the case of an injection, a solution for injection is prepared using a carrier or the like formed of a salt solution, a glucose solution, or a mixture of a salt solution and a glucose solution.

Even in these parenteral agents, one or more supplementary components selected from antiseptics, preservatives, excipients, disintegrators, lubricants, binders, surfactants, plasticizers, and the like listed for the oral agent can be used.

Although the concentration of the glutathione or a salt thereof in the agent for elevating NO concentration according to the present invention is suitably selected depending on the product form or the type of formulation, or the effect or the like expected by ingestion or administration of the product or formulation, the concentration is usually 0.1% by weight to 100% by weight, preferably 0.5% by weight to 80% by weight, and particularly preferably 1% by weight to 70% by weight, in terms of glutathione or a salt thereof.

Although the amount of ingestion or administration and the number of ingestion or administration of the agent for elevating NO concentration according to the present invention vary depending on the ingestion or administration form, the age, the body weight, or the nature or the severity of a symptom to be treated of a person in need of ingestion or administration, usually, administration is performed once or several times a day such that the dose usually becomes 10 mg to 10 g, preferably 50 mg to 50 g, and particularly preferably 100 mg to 1 g per day for an adult, in terms of glutathione or a salt thereof.

The ingestion or administration period is not particularly limited, but is usually one day to one year, preferably three days to six months, and more preferably one week to three months.

The agent for elevating NO concentration according to the present invention can be used to exhibit prevention or amelioration of a vascular endothelial malfunction-related symptom, or vasodilation and blood flow-promoting effects through a higher NO concentration elevating action in vivo. Since prevention or amelioration of a vascular endothelial malfunction-related symptom, or effective vasodilation effective blood flow-promoting effects can be expected from the agent for elevating NO concentration according to the present invention, the agent can be applied to prevention or amelioration of an ischemic disease, exercise performance improvement, muscle metabolism improvement, lipid accumulation suppression, skin quality improvement, memory and learning ability improvement, attention concentration improvement, shoulder stiffness amelioration, amelioration of excessive sensitivity to cold, or swelling suppression.

The method of the present invention can be used for preventing or ameliorating the symptom by the agent for elevating NO concentration according to the present invention being ingested by a subject in need of elevating the NO concentration in the body, a subject who desires a physiological effect by elevation of the NO concentration, or a subject who exhibits the symptom or being administered to the subject.

In the present invention, the glutathione or a salt thereof can be used for the manufacture of the agent for elevating NO concentration.

In addition, the present invention includes a method for elevating the NO concentration. The method of the present invention comprises a step of having a subject in need of elevating the NO concentration ingest glutathione or a salt thereof in a sufficient amount to elevate the NO concentration of the subject or administering glutathione or a salt thereof in the sufficient amount to the subject.

In addition, the present invention includes a method for preventing or ameliorating a vascular endothelial malfunction. The method of the present invention comprises a step of having a subject in need of preventing or ameliorating the vascular endothelial malfunction ingest glutathione or a salt thereof in a sufficient amount to prevent or ameliorate the vascular endothelial malfunction or administering glutathione or a salt thereof in the sufficient amount to the subject.

In addition, the present invention includes a method for dilating blood vessels or promoting blood flow. The method of the present invention comprises a step of having a subject in need of dilating blood vessels or promoting blood flow ingest glutathione or a salt thereof in a sufficient amount to dilate blood vessels or promote blood flow or administering glutathione or a salt thereof in the sufficient amount to the subject.

Hereinafter, the present invention will be described in more detail with reference to Examples; however, the present invention is not limited thereto. Test Examples in which NO concentration elevating effect of glutathione is examined will be shown below. Test Examples Eight-week-old male SD rats were purchased from Japan SLC, Inc. Under isoflurane anesthesia, a catheter was indwelled in a carotid artery, and after awakening, the rats were acclimatized for one week. The rats were allowed to freely ingest solid feed (CE-2, manufactured by Clea Japan, Inc.) and tap water, and reared at a temperature of 20° C. to 24° C. and a humidity of 50% to 60% in a light and darkness cycle for 12 hours. In addition, reduced glutathione manufactured by Kyowa Hakko Bio Co., Ltd. was used. After acclimatization, a blood sample of a baseline was taken using the catheter indwelled in the carotid artery. Next, purified water (control group), 25 mg/kg/day of reduced glutathione (glutathione-25 mg/kg group), or 50 mg/kg/day of reduced glutathione (glutathione-50 mg/kg group) was forcibly administered orally to each rat once a day for three days, and blood collection was performed immediately before the last administration and for 4 hours after the last administration over time using the catheter indwelled in the carotid artery. Moreover, the rats were fasted for 16 hours before the last administration. After obtaining blood plasma from the blood sample, the concentrations of nitrite ($NO_2^-$) and nitrate ($NO_3^-$) which are stable NO metabolites in the blood were determined by a HPLC method (ENO-20, EICOM). That is, the NO concentration in the blood was expressed as NOx which is the sum of these, and the amount of increase in the NOx from the baseline at the time of each blood collection was calculated.

Figure 2:
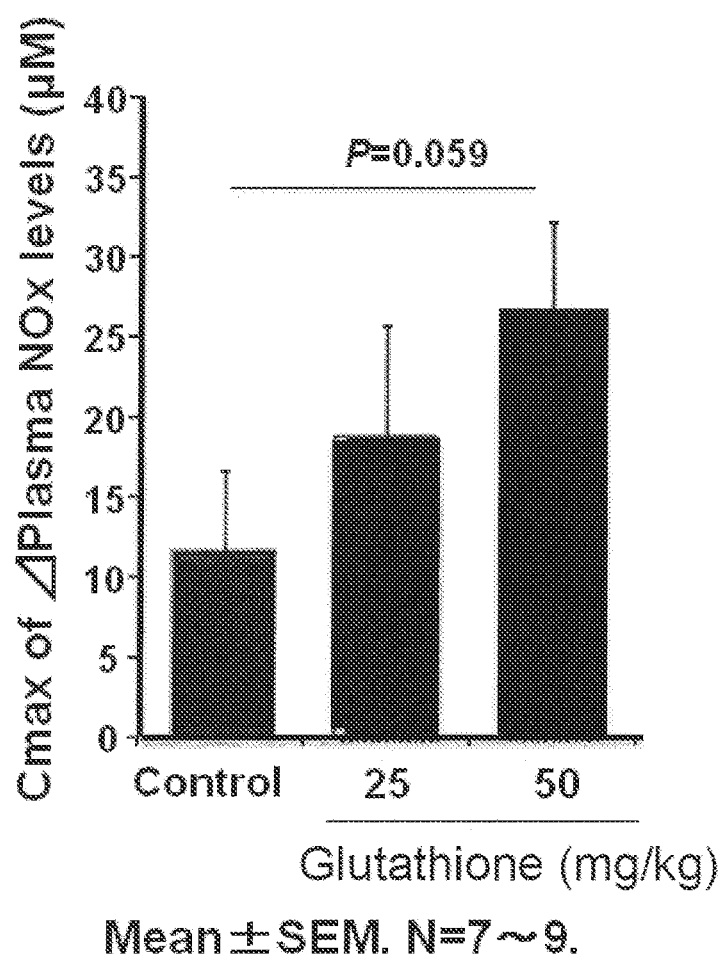
FIG. 2 shows a maximum concentration (Cmax) in an increase of the NOx concentration in blood after the reduced glutathione is administered orally to the rats.

As shown in FIG. 1, in the glutathione-50 mg/kg group, the amount of increase in the NOx concentration in blood plasma from the baseline was significantly increased compared to that of the control group. In addition, the same tendency was also observed in the glutathione-25 mg/kg group. As shown in FIG. 2, it was observed that the maximum blood concentration (Cmax) in the amount of increase in the NOx concentration was also significantly increased in a dose-dependent manner by glutathione administration compared to the control group.

From this fact, it was shown for the first time that the NO concentration in the blood is effectively elevated by administering glutathione, and it was shown that the agent for elevating NO concentration according to the present invention is excellent. Hereinafter, Examples of the present invention will be described.

Example 1

Manufacture of Tablet Containing Glutathione

Reduced glutathione (120 kg), cyclic oligosaccharide (19 kg), cellulose (57 kg), and pullulan (1 kg) were granulated using a fluidized bed granulating and drying machine. The obtained granules and calcium stearate (3 kg) were mixed using a conical blender, and the resultant product was compression-molded using a rotary type compression molding machine, whereby tablets were manufactured.

Example 2

Manufacture of Enteric Tablet Containing Glutathione

The surfaces of the tablets manufactured in Example 1 are coated with a shellac solution, whereby enteric tablets were manufactured.

Example 3

Manufacture of Enteric Capsule Containing Glutathione

Reduced glutathione (120 kg), cyclic oligosaccharide (19 kg), cellulose (57 kg), calcium stearate (3 kg), and pullulan (1 kg) are mixed using a conical blender. The mixture obtained by stirring to mix the obtained mixture (20 kg) and silicon dioxide (0.2 kg) is put into a capsule filling machine, and packed into hard capsules, whereby hard capsules are obtained. The surfaces of the obtained hard capsules are coated with a zein solution, whereby enteric capsules were manufactured.

Example 4

Manufacture of Drink Containing Glutathione (1)

Oxidized glutathione (1.28 kg), erythritol (3 kg), citric acid (0.05 kg), an artificial sweetener (3 g), and a flavor (0.06 g) are stirred to dissolve in water (50 L) at 70° C., and the resultant product is adjusted to pH 3.3 with citric acid, sterilized by a plate sterilization, put into a bottle, and subjected to pasteurizer sterilization, whereby a drink is manufactured.

Example 5

Manufacture of Drink Containing Glutathione (2)

Oxidized glutathione (20 mg), arginine (20 mg), and suitable amounts of fructose glucose liquid sugar, salt, citric acid, a flavor, sodium citrate, calcium lactate, iron pyrophosphate, calcium gluconate, potassium chloride, magnesium chloride, and a sweetener are mixed, whereby a drink (555 mL) is manufactured.

Example 6

Manufacture of Drink Containing Glutathione (3)

Oxidized glutathione (100 mg), arginine (100 mg), alanine (2.5 mg), glycine (2.5 mg), leucine (2.5 mg), isoleucine (1.3 mg), valine (1.3 mg), and suitable amounts of a flavor and a sweetener are mixed, whereby a drink (300 mL) is manufactured.

Example 7

Manufacture of Toner Containing Glutathione

Ethanol (10.0% by weight), reduced glutathione (2.0% by weight), 1,3-butylene glycol (5.0% by weight), and purified water (83.0% by weight) are mixed, whereby a toner is manufactured.

Example 8

Manufacture of Cream Containing Glutathione

Polyethylene glycol (PEG55), monostearate (2.00% by weight), self-emulsifying glyceryl monostearate (5.00% by weight), cetyl alcohol (4.00% by weight), squalane (6.00% by weight), triglyceryl 2-ethylhexanoate (6.00% by weight), 1,3-butylene glycol (7.00% by weight), L-histidine (3.00% by weight), reduced glutathione (1.00% by weight), and purified water (66.00% by weight) are mixed, whereby a cream is manufactured.

Example 9

Manufacture of Lotion Containing Glutathione

Oxidized glutathione (3.00% by weight), L-serine (1.00% by weight), water-soluble collagen (1.00% by weight; 1% aqueous solution), sodium citrate (0.10% by weight), citric acid (0.05% by weight), licorice extract (0.20% by weight), 1,3-butylene glycol (3.00% by weight), and purified water (91.65% by weight) are mixed, whereby a lotion is manufactured.

Example 10

Manufacture of Facial Mask Containing Glutathione

Polyvinyl alcohol (13.00% by weight), L-aspartic acid (1.00% by weight), reduced glutathione (5.00% by weight), lauroyl hydroxyproline (1.00% by weight), water-soluble collagen (2.00% by weight; 1% aqueous solution), 1,3-butylene glycol (3.00% by weight), ethanol (5.00% by weight), and purified water (70.00% by weight) are mixed, whereby a mask is manufactured.

Example 11

Manufacture of Beauty Lotion Containing Glutathione

Hydroxyethyl cellulose (12.0% by weight; 2% aqueous solution), xanthan gum (2.0% by weight; 2% aqueous solution), reduced glutathione (2.0% by weight), 1,3-butylene glycol (6.0% by weight), concentrated glycerin (4.0% by weight), sodium hyaluronate (5.0% by weight; 1% aqueous solution), and purified water (69.0% by weight) are mixed, whereby a beauty water is manufactured.

The invention claimed is:

1. A method for elevating nitric oxide (NO) concentration comprising orally administering glutathione or a salt thereof at a dose of 10 mg to 10 g per day to elevate the NO concentration of a subject who desires improvement in muscle metabolism, but does not have a vascular endothelial malfunction,
wherein the glutathione or a salt thereof is orally administered as a tablet, a powder, a granule, a pill, an infusion decoction, a capsule, a drink with glutathione dissolved therein, a drink with a salt of glutathione dissolved therein, a solution, an elixir, an extract, a tincture, or a fluid extract, and
wherein the elevated NO concentration causes muscle metabolism improvement in the subject.

2. A method for dilating blood vessels or promoting blood flow in a subject comprising orally administering glutathione or a salt thereof at a total dose of 10 mg to 10 g per day to dilate blood vessels or promote blood flow in a subject who desires improvement in muscle metabolism, but does not have a vascular endothelial malfunction,
wherein the glutathione or a salt thereof is orally administered as a tablet, a powder, a granule, a pill, an infusion decoction, a capsule, a drink with glutathione dissolved therein, a drink with a salt of glutathione dissolved therein, a solution, an elixir, an extract, a tincture, or a fluid extract, and
wherein the dilation of the blood vessels or promotion of blood flow causes muscle metabolism improvement in the subject.

3. The method for elevating NO concentration according to claim 1, wherein the glutathione or a salt thereof is reduced glutathione or a salt thereof, or/and oxidized glutathione or a salt thereof.

4. The method for dilating blood vessels or promoting blood flow in a subject according to claim 2, wherein the glutathione or a salt thereof is reduced glutathione or a salt thereof, or/and oxidized glutathione or a salt thereof.

* * * * *

UNITED STATES PATENT AND TRADEMARK OFFICE
CERTIFICATE OF CORRECTION

PATENT NO. : 11,654,125 B2
APPLICATION NO. : 14/762108
DATED : May 23, 2023
INVENTOR(S) : Masahiko Morita et al.

It is certified that error appears in the above-identified patent and that said Letters Patent is hereby corrected as shown below:

In the Claims

In Claim 1, at Column 12, Line 8, "subj ect" should read "subject".

Signed and Sealed this
First Day of August, 2023

Katherine Kelly Vidal
*Director of the United States Patent and Trademark Office*